United States Patent
Jenny et al.

(10) Patent No.: US 7,049,087 B2
(45) Date of Patent: May 23, 2006

(54) METHOD FOR MANUFACTURING A TISSUE FACTOR-BASED PROTHROMBIN TIME REAGENT

(75) Inventors: Richard Jenny, Essex Junction, VT (US); Paul E. Haley, Jericho, VT (US); Brian Earp, San Jose, CA (US)

(73) Assignee: Lifescan, Inc., Milpitas, CA (US)

( * ) Notice: Subject to any disclaimer, the term of this patent is extended or adjusted under 35 U.S.C. 154(b) by 460 days.

(21) Appl. No.: 10/288,249

(22) Filed: Nov. 5, 2002

(65) Prior Publication Data

US 2004/0086953 A1    May 6, 2004

(51) Int. Cl.
*C12Q 1/56*    (2006.01)
(52) U.S. Cl. .................................................... 435/13
(58) Field of Classification Search .................. 435/13
See application file for complete search history.

(56) References Cited

U.S. PATENT DOCUMENTS

| | | | |
|---|---|---|---|
| 5,314,695 A | 5/1994 | Brown | |
| 5,399,487 A | 3/1995 | Butenas et al. | |
| 5,418,141 A | 5/1995 | Zweig et al. | |
| 5,625,036 A | 4/1997 | Hawkins et al. | |
| 6,100,072 A | 8/2000 | Brucato et al. | |
| 6,183,979 B1 | 2/2001 | Lee et al. | |
| 2002/0110922 A1 | 8/2002 | Shartle et al. | |

FOREIGN PATENT DOCUMENTS

| EP | 0 915 157 | 5/1999 |
|---|---|---|
| WO | WO 93/07492 | 4/1993 |

OTHER PUBLICATIONS

Ollivon, M. et al., "Vesicle reconstitution from lipid-detergent mixed micelles", Biochimica Et Biophysica ACTA Biomembranes, Amsterdam, NL, vol. 1508, No. 1-2, Nov. 2000, pp. 34-50.

Kario, K. et al., "Fluorogenic assay of activated factor VII. Plasma factor VIIa levels in relation to arterial cardiovascular diseases in Japanese", Arteriosclerosis Thrombosis: A Journal of Vascular Biology/American Heart Assoc., USA, vol. 14, No. 2, Feb. 1994.

Nemerson, Y., "Tissue Factor and Hemostasis", BLOOD, The Journal of The American Society of Hematology, vol. 71, No. 1, Jan. 1988, pp. 1-8.

Hirsch, Jack et al., "Oral Anticoagulants: Mechanism of Action, Clinical Effectiveness, and Optimal Therapeutic Range", Sixth ACCP Consensus Conference on Antithrombotic Therapy, CHEST, vol. 119, No. 1, Suppl., Jan. 2001, pp. 8S-21S.

Chen, P.S. et al., "Microdetermination of Phosphorus", Analytical Chemistry, vol. 58, No. 11, Nov. 1956, pp. 1756-1758.

European Search Report, dated Feb. 24, 2004, for European Application No. EP 03 25 6966.

*Primary Examiner*—Sandra E. Saucier

(57) ABSTRACT

A method for manufacturing a tissue factor-based prothrombin-time reagent includes combining predetermined quantities of tissue factor (TF), phospholipid and detergent-containing buffer to create a TF/phospholipid mixture. In this combining step, the quantity of TF is predetermined based upon its measured TF activity. Next, the detergent is removed from the TF/phospholipid mixture to produce an essentially detergent-free TF/phospholipid mixture that is useful as a tissue factor-based PT reagent. The method can include the use of hydrophobic resin that has been pre-screened based on phospholipid recovery to accomplish the removal of the detergent.

11 Claims, 1 Drawing Sheet

METHOD FOR MANUFACTURING A TISSUE FACTOR-BASED PROTHROMBIN TIME REAGENT

BACKGROUND OF INVENTION

1. Field of the Invention

The present invention relates, in general, to the field of prothrombin time (PT) reagents and, in particular, to a method for manufacturing PT reagents.

2. Description of the Related Art

Blood coagulation tests may be performed for a variety of purposes, including determination of the bleeding susceptibility of patients undergoing surgery and monitoring of patients undergoing anticoagulant therapy for prevention of blood clots. A number of coagulation tests are currently in use, one of which is the "prothrombin time" (PT) test. The PT test relies upon activation of the extrinsic coagulation pathway by thromboplastin that has been added to a blood sample undergoing the PT test. Activation of the extrinsic coagulation pathway leads to the production of thrombin, a proteolytic enzyme that catalyzes the conversion of fibrinogen to fibrin, a catalysis that is essential to the clotting process.

Thromboplastin, also known as tissue factor (TF), is a membrane associated glycoprotein that forms a complex with factor VIIa. The factor VIIa/TF complex initiates the blood coagulation process. Once formed, the factor VIIa/TF complex activates a series of specific enzymes that are involved in the extrinsic and intrinsic pathways of the coagulation cascade, ultimately leading to the formation of thrombin, fibrin, platelet activation, and finally clot formation. For a related discussion, see Nemerson, Yale, *Tissue Factor and Hemostasis*, Blood, 71, pp.1–8 (1988).

Conventional PT tests utilize the above-described series of enzymatic events in an in vitro environment and under controlled conditions to diagnose dysfunctions or deficiencies in the blood coagulation system of patients. The time period it takes for clot formation to occur is referred to as the Prothrombin Time or PT value.

Different types of thromboplastins can either enhance or diminish the ability of a PT test to discriminate between blood samples having different prothrombin times. Thromboplastins with greater discrimination are termed "more sensitive". The liquid phase sensitivity of a thromboplastin preparation is graded by use of the International Sensitivity Index (ISI). An ISI value can be obtained by plotting, on a logarithmic scale, the prothrombin time value obtained with a given thromboplastin lot versus the prothrombin time values obtained with a standardized reference lot of thromboplastin. The ISI value of the given thromboplastin lot is the slope of the resulting line multiplied by the ISI of the standardized reference lot of thromboplastin. More sensitive thromboplastins have lower ISI numbers around 1.0 and less sensitive thromboplastins have higher ISI numbers, typically around 2.0 to 3.0.

For use in PT testing, a highly sensitive PT reagent with an ISI of approximately 1.0 is considered most beneficial and suitable since, with an ISI of 1.0, the calculation of an International Normalized Ratio (INR) is simplified and precise. One skilled in the art will recognize that use of the INR can compensate for thromboplastin variation due to differences in sensitivity. INR is calculated using the following equation (see Hirsh et al., *Oral Anticoagulants: Mechanism of Action, Clinical Effectiveness, and Optimal Therapeutic Range*, Chest 2001; 119:8S–21S):

$$INR = (\text{patient } PT/\text{mean normal } PT)^{ISI}$$

where:
- patient PT=the prothrombin time of a patient's blood sample, and
- mean normal PT (or MNPT)=the mean prothrombin time of blood samples from at least twenty normal (reference) sample donors.

Conventional methods for manufacturing PT reagents generally use TF from natural or recombinant sources, natural or synthetic phospholipids, calcium and a buffer composition. U.S. Pat. No. 5,314,695, which is fully incorporated herein by reference, discloses a method for manufacturing PT reagents. The reagents include liposome compositions, in which natural or recombinant tissue factor is associated with, and inserted into, the liposomes' phospholipid bilayer. In the PT reagent manufacturing methods described therein, a determination of the quantity of TF employed in manufacturing the PT reagent is determined entirely on a mass to volume basis.

U.S. Pat. No. 5,625,036, which is fully incorporated by reference, discloses a PT reagent for use in PT testing and a method for creating lipid vesicles containing tissue factor. This PT reagent utilizes recombinant human tissue factor, phospholipids of a natural or synthetic origin, a buffer composition and calcium ions. Stabilizers and salts may also be utilized in the PT reagent.

Use of dried thromboplastin in PT test devices is described in U.S. Pat. No. 5,418,141 and U.S. patent application Ser. No. 2002/0110922, both of which are fully incorporated herein by reference. U.S. Pat. No. 5,418,141 describes the use of recombinant thromboplastins in dry reagent prothrombin time assays. The recombinant thromboplastins are employed for the purpose of improving test precision. In addition, this patent compares recombinant thromboplastin to natural thromboplastins, which, when used in dry reagent PT assays, are less sensitive and result in less precise ISI values. In U.S. patent application No. 2002/0110922, a fluidic test device is described that incorporates thromboplastin into three measurement areas, one of which is used for measuring the PT time of a blood sample. The other two measurement areas are used as control areas, thereby increasing the reliability of PT times measured using the fluidic test device. The control areas contain components in addition to thromboplastin in order to partially or completely overcome the effect of an anticoagulant present in the blood sample.

With experience, it has become apparent that conventional methods for manufacturing PT reagents do not reproducibly yield a suitably sensitive PT reagent. Still needed in the field, therefore, is a method for manufacturing a PT reagent that reproducibly yields a suitably sensitive PT reagent. In addition, the method should be simple and provide for acceptance testing of the manufactured PT reagent.

SUMMARY OF INVENTION

The present invention provides a method for manufacturing a tissue factor-based prothrombin time (PT) reagent that reproducibly yields a suitably sensitive tissue factor-based PT reagent. In addition, the method is simple and provides for acceptance testing of the manufactured tissue factor-based PT reagent.

In arriving at the present invention, it was recognized that the reproducibility (e.g., lot-to-lot variation) and suitability (e.g., sensitivity) of tissue factor-based PT reagents is determined by a variety of previously unrecognized critical factors during manufacturing. These critical factors include (i) the specific activity of the TF employed during manufacturing; and (ii) the phospholipid concentration both during manufacturing and in the final tissue-factor-based PT reagent. Since the activity of TF and phospholipid concentration are both critical factors, the ratio of active TF (measured as units of activity) to phospholipid concentration employed during manufacturing is also of interest. Embodiments of methods according to the present invention, therefore, include steps such that one or more of the critical factors is controlled. Such control provides a manufacturing method (process) that reproducibly yields a suitable sensitive tissue factor-based PT reagent.

A method for manufacturing a tissue factor-based PT reagent according to an exemplary embodiment of the present invention includes combining predetermined quantities of tissue factor (TF), phospholipid and detergent-containing buffer to create a TF/phospbolipid mixture. In this combining step, the quantity of TF is predetermined based upon its measured TF activity. Next, the detergent is removed from the TF/phospholipid mixture to produce an essentially detergent-free TF/phospholipid vesicle mixture. Such a detergent-free TF/phospholipid vesicle mixture is useful as a tissue factor-based PT reagent.

BRIEF DESCRIPTION OF DRAWINGS

A better understanding of the features and advantages of the present invention will be obtained by reference to the following detailed description that sets forth illustrative embodiments, in which the principles of the invention are utilized, and the accompanying drawings of which.

DETAILED DESCRIPTION OF THE INVENTION

Figure 1:
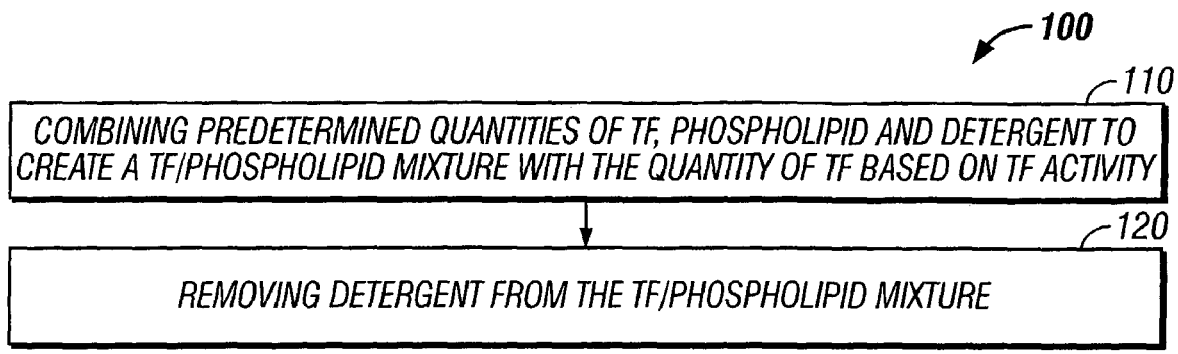
FIG. 1 is a flow chart illustrating a sequence of steps in a process according to one exemplary embodiment of the present invention.

FIG. 1 is a flow chart of a process 100 for manufacturing a tissue factor-based PT reagent in accordance with an exemplary embodiment of the present invention. Process 100 includes combining predetermined quantities of tissue factor (TF), phospholipid and a detergent-containing buffer to create a TF/phospholipid mixture, as set forth in step 110. The quantity of TF is predetermined in this step based upon its measured TF activity.

The tissue factor employed in processes according to the present invention, including process 100, can be any suitable tissue factor known to one skilled in the art. Suitable tissue factors can include, for example, tissue factors from natural or synthetic sources. Use of recombinant tissue factor (rTF) is particularly beneficial in providing a tissue factor-based PT reagent that is highly sensitive when employed in, for example, a dry state.

The TF activity of the predetermined quantity of tissue factor can be measured using any suitable TF activity assay known to those skilled in the art and/or specifically developed for use in conjunction with methods according to the present invention. Those skilled in the art will recognize that such TF activity assays measure TF functional activity and not simply the quantity of TF.

Particularly beneficial and simple TF activity assays that can be employed to measure TF activity utilize a fluorogenic substrate to measure the ability of TF to function as a cofactor to factor VIIa. In doing so, such a TF activity assay determines the capacity of factor VIIa to cleave a fluorogenic substrate (e.g., the fluorogenic substrate 6-peptidy-lamino-1-naphthalenesulfonomides in the presence of tissue factor. In such an assay, the binding of factor VIIa to TF enhances this capacity by approximately 100 fold. Comparison of a subject TF preparation to a standard preparation of tissue factor (available from, for example, the World Health Organization Standard) enables an activity determination of the subject TF preparations.

In the circumstance that TF activity has been measured as the ability for TF to function as a cofactor to factor VIIa, it has been ascertained that adding TF such that the TF/phospholipids mixture has a TF activity in the range of 9000 to 18000 Units per liter is particularly beneficial in terms of providing a reproducible and sensitive tissue factor-based PT reagent. In this circumstance, the TF activity units are defined by assigning a TF activity of 1 Unit/ml to WHO standard thromboplastin reconstituted according to instructions supplied by the WHO. One skilled in the art will recognize that the range of 9000 to 18000 Units per liter has been specified in relationship to the TF/phospholipids mixture and not the detergent-free TF/phospholipids vesicle mixture.

The detergent-containing buffer employed in step 110 can be any suitable detergent-containing buffers known to those skilled in the art. For example, the detergent containing buffer can be a 100 mM 3-[(3-cholamidopropyl)-dimethylammonio]-1-propanesulfonate (CHAPS) buffer and/or CHAPS/Bovine Gamma Globulin (BGG) buffer. The phospholipids utilized in step 110 can be any suitable phospholipids or mixture of phospholipids known to one skilled in the art. For example, a phospholipid mixture containing phosphatidylcholine, phosphatidyl-glycerol, phosphatidylethanolamine, and phosphatidylserine can be used.

Combining step 110 can include, for example, adding the predetermined quantity of TF to a mixture of phospholipid and detergent-containing buffer. Such a combining step provides for the simple and successful incorporation of TF into the phospholipid and detergent-containing buffer mixture). In PT reagent manufacturing methods known in the art, the addition of TF to such a phospholipid and detergent-containing mixture is done entirely on a mass to volume basis (see, for example, U.S. Pat. No. 5,314,695). Using this conventional approach, the mass quantity of TF added during manufacturing of a PT reagent is known, but nothing is known about the functional quality (i.e., activity) of the added TF.

Next, the detergent is removed from the TF/phospholipid mixture to provide an essentially detergent-free TF/phospholipid vesicle mixture, as set forth in step 120 of FIG. 1. One skilled in the art will recognize that such a detergent-free TF/phospholipid vesicle mixture can serve as a tissue factor-based PT reagent.

The removal of the detergent can be accomplished using any suitable technique known to those skilled in the art. Suitable techniques include, for example, adding a hydrophobic resin (e.g., XAD-16 hydrophobic resin) to the TF/phospholipid mixture, incubating the TF/phospholipid mixture and the added resin until the TF/phospholipid mixture is essentially free of detergent; and then removing said hydrophobic resin from the TF/phospholipid mixture. Other suitable techniques include gradual removal of the detergent by dialysis or by tangential flow filtration.

The essentially detergent-free TF phospholipid vesicle mixture can include a functionally insignificant amount of detergent while still being considered "essentially detergent-free." The concentration of detergent that is considered functionally insignificant can be determined by one of skill in the art through routine experimentation. By way of example, 0.2 mM or less of CHAPs detergent was determined to be functionally insignificant in certain embodiments of the present invention.

As explained above, embodiments of the present invention can involve the addition of a predetermined quantity of TF to a phospholipid and detergent-containing buffer mixture. In such embodiments, the phospholipid can be mixed with a non-denaturing zwitterionic detergent to create a phospholipid and detergent-containing mixture that includes mixed micelles of phospholipid and detergent. An exemplary non-denaturing zwitterionic detergent is 3-[(3-cholamidopropyl)dimethylammonio]-1-propanesulfonate (CHAPS).

Any suitable hydrophobic resin can be employed to remove detergent in methods according to the present invention, including but not limited to, Amberlite XAD-16, which is commercially available from Sigma Chemicals, St. Louis, Mo. Those skilled in the art will recognize that the removal of detergent in processes according to the present invention can, for example, cause the phospholipids to form unilamellar vesicles, into which TF becomes incorporated by virtue of the TF's membrane binding domain. The resultant essentially detergent-free TF/phospholipid vesicle mixture is a uniform mixture of unilamellar vesicles containing TF, some of which is oriented with an active portion exposed on the surface of the unilamellar vesicles. The effectiveness of such a tissue factor-based PT reagent to serve as a cofactor for factor VIIa is believed to be dictated by the number of functional TF molecules available at the surface of the vesicles. The addition of TF based on a conventional mass-to-volume basis merely assures the quantity of such TF, but not the functional quality thereof. By basing the predetermined quantity of TF on activity instead, the amount of functional TF available at the surface of the vesicles can be more precisely controlled and, in effect, "standardized" from lot-to-lot of the tissue factor-based PT reagent.

In addition to the amount of functional TF, it has been recognized that the quantity of phospholipid employed during the manufacturing of a tissue factor-based PT reagent also influences its suitability and reproducibility. It has been further recognized that the amount of phospholipid present in the essentially detergent-free TF/phospholipid vesicle mixture is linked to phospholipid loss during removal of the detergent.

To control the amount of phospholipid present in the tissue factor-based PT reagent, an acceptance test for phospholipid concentration can be employed in processes according to the present invention. For example, the processes can employ steps to (i) measure the total phospholipid concentration of the essentially detergent-free TF/phospholipid vesicle mixture; and (ii) determine acceptability of the essentially detergent-free TF/phospholipid vesicle mixture for use as a tissue factor-based PT reagent based on the measured total phospholipid concentration.

The total phospholipid concentration can be measured using, for example, assays for inorganic phosphate that are well know in the art and for which procedures are readily available (see Chen et al., *Microdetermination of Phosphorus*, Analytical Chemistry, 28(11), 1756–1758 (1956)). Since phospholipid is the only potential significant source of inorganic phosphate in processes according to the present invention, the molar concentration of phosphate is directly proportional to the molar concentration of phospholipid in a sample. A particularly beneficial phospholipid concentration (measured as inorganic phosphate) in the essentially detergent-free TF/phospholipid vesicle mixture is in the range of from 2.5 to 5.0 mM. An even more beneficial phospholipid concentration is in the range of ^3.0 to ^5.0 mM, with a 3.8 mM phospholipid concentration being exceptionally beneficial.

In another exemplary embodiment of processes according to the present invention, resin employed in the removal of detergent is prescreened prior to use in the process. Such prescreening is based on a percent recovery of phospholipid (see EXAMPLE 1 below) and can, for example, employ the inorganic assays described above. Prescreening according to embodiments of the present invention can beneficially control loss of phospholipid during a detergent removal step and serve to insure that the essentially detergent-free TF/phospholipid vesicle mixture contains a controlled concentration of phospholipid.

EXAMPLE 1

Pre-screening of Hydrophobic Chromatographic Resin for Use in Manufacturing a Tissue Factor-Based PT Reagent The following study demonstrates an exemplary technique by which hydrophobic resin lots were successfully prescreened, based on percent recovery of phospholipid, for use in a tissue factor-based PT reagent manufacturing process according to the present invention. In order to pre-screen the hydrophobic resin lots, 4.95 mM of a solubilized phospholipid mixture (containing phosphatidylcholine, phosphatidyl-glycerol, phosphatidylethanolamine and phosphatidylserine, available from Avanti Polar Lipids, Alabaster, Ala.) and 30 grams of Amberlite XAD-16 hydrophobic resin (commercially available from Sigma Chemical Company, St. Louis, Mo.) were combined in 100 mL of 20 mM Tris and 150 mM NaCl (TBS) buffer containing 0.8% glycine, 150 mM trehalose, 100 mM CHAPS and 0.05% sodium azide. The pH of the buffer was 7.4.

The phospholipid and hydrophobic resin were mixed for approximately one hour at room temperature. The mixture's supernatant was collected and assayed for phospholipid (measured as inorganic phosphate using a conventional inorganic phosphate assay). The percent (%) recovery of phospholipid was then calculated from the inorganic phosphate assay results. Data from the testing of six lots of hydrophobic resin are reported in Table 1. Tissue factor-based PT reagent lots prepared with resin lot number 2 consistently failed final release testing. Based on the data of Table 1 and an understanding of the measurement accuracy associated with percent (%) recovery, only those lots of hydrophobic resin yielding a 75% to 95% recovery of phospholipid were deemed acceptable for use in manufacturing the tissue factor-based PT reagent.

TABLE 1

Summary of Phospholipid Recovery Data for Resin Lots

| Lot of Resin | Final Inorganic Phosphate Concentration (mM) | % Recovery |
|---|---|---|
| 1 | 4.6 | 93 |
| 2 | 3.3 | 67 |
| 3 | 4.4 | 88 |
| 4 | 4.4 | 88 |
| 5 | 4.1 | 82 |
| 6 | 3.9 | 79 |

EXAMPLE 2

Exemplary Process for Manufacturing a Tissue Factor-Based PT Reagent

Lyophilized phospholipids (1.5 grams) obtained from Avanti Polar Lipids (Alabaster, Ala.) at a mole ratio of 67:16:10:7 (phosphatidyl choline: phosphatidyl glycerol: phosphatidyl ethanolamine: phosphatidyl serine) were solubilized in 100 mL of TBS buffer containing 0.8% glycine, 150 mM trehalose, 100 mM CHAPS and 0.05% sodium azide. At all steps in this exemplary process, the reagent solution was mixed while being maintained at 30–37° C. Based upon the assayed inorganic phosphate concentration of this solubilized phospholipid, 2.25 mmol of solubilized phospholipid was removed for further processing.

The volume containing 2.25 mmol of phospholipid that was removed for further processing was adjusted to 100 ml by the addition of TBS buffer containing 0.8% glycine, 150 mM trehalose, 100 mM CHAPS and 0.05% sodium azide. Fifty milliliters (50 ml) of a bovine gamma globulin solution (0.1% in TBS containing 20 mM CHAPS, 0.8% glycine, 150 mM trehalose and 0.05% sodium azide) was then added to the solubilized phospholipid mixture. Next, rTF (in TBS containing 10 mM CHAPS) and additional buffer (TBS buffer containing 0.8% glycine, 150 mM trehalose and 0.05% sodium azide) was added to the phospholipid mixture to yield 500 ml of TF/phospholipid mixture with a rTF concentration of 13,500 units/L.

After the rTF/phospholipid mixture was mixed for one hour, 150 grams of pre-screened (per the exemplary technique described above) and pre-washed XAD-16 hydrophobic resin was added. After mixing 3.5 hours, the rTF/phospholipid mixture was filtered to remove the hydrophobic resin and stored at 2–8° C. The addition of resin, incubation and removal of the resin produced an essentially detergent-free rTF/phospholipid vesicle mixture (i.e., tissue factor-based PT reagent).

The tissue factor-based PT reagent was then assayed to determine its final phospholipid concentration (measured as inorganic phosphate). The tissue factor-based PT reagent was also coated and dried into a test strip format. The ISI and MNPT of each multiple tissue factor-based PT reagent lots were then determined by testing test strips with at least 100 whole blood capillary samples, at least 20 of which were from normal patients and at least 80 of which were from patients on oral anticoagulant therapy. The ISI value was obtained by plotting, on a logarithmic scale, the prothrombin time obtained with a lot in question versus the prothrombin time values obtained with a standardized lot of thromboplastin tested on a reference instrument. The ISI value is the slope of the resulting line multiplied by the ISI of the reference thromboplastin. The MNPT is the mean prothroimbin time of at least twenty normal donors.

Table 2 shows the ISI and MNPT for tissue factor-based PT reagent lots manufactured using methods that encompassed a relatively wide range of added rTF and that utilized a resin that was not prescreened. An acceptable range for ISI and MNPT is 1.0–1.3 and 7.0 to 9.0 seconds, respectively. The data in Table 2 indicate that certain combinations of TF and phospholipid cause the lots to fail the ISI and MNPT release criteria. For example, when both a low TF and a low phospholipid concentration are used to make PT reagent, the resulting ISI is above the acceptable range.

TABLE 2

Summary of ISI and MNPT for rTF-based PT Reagent Lots Manufactured Using Resin that had not been Prescreened.

| RTF-based PT Reagent Lot Number | rTF Concentration (U/L) in the TF/phospholipid mixture | Inorganic Phosphate Concentration (mM) | ISI | MNPT (seconds) | Pass/Fail |
|---|---|---|---|---|---|
| 1 | 9,250 | 1.93 | 1.37 | 8.88 | F |
| 2 | 9,250 | 2.56 | 1.36 | 9.72 | F |
| 3 | 9,250 | 2.78 | 1.27 | 8.82 | P |
| 4 | 9,218 | 3.02 | 1.18 | 8.17 | P |
| 5 | 9,248 | 3.80 | 1.23 | 8.36 | P |
| 6 | 9,000 | 5.20 | 1.10 | 8.03 | P |
| 7 | 11,500 | 2.42 | 1.25 | 8.62 | P |
| 8 | 13,250 | 3.00 | 1.23 | 7.95 | P |
| 9 | 13,856 | 3.40 | 1.08 | 8.12 | P |
| 10 | 13,500 | 3.60 | 1.11 | 7.66 | P |
| 11 | 13,500 | 3.90 | 1.16 | 7.84 | P |
| 12 | 17,000 | 1.92 | 1.32 | 7.92 | F |
| 13 | 17,244 | 3.60 | 1.09 | 7.39 | P |
| 14 | 18,000 | 3.80 | 1.12 | 7.42 | P |

Table 3 summarizes the ISI and MNPT results for tissue factor-based PT reagent lots manufactured according to an exemplary process (described above) and adjusted to provide various rTF and phospholipid concentrations. The results in Table 3 indicate that tissue factor-based PT reagent lots manufactured according to the present invention include consistent (i.e., reproducible) amounts of rTF and phosopholipid and have more reproducible and suitable ISI and MNPT values than lots manufactured using conventional methods. None of the lots of Table 3 failed the ISI and MNPT criteria.

TABLE 3

Summary of ISI and MNPT for rTF-based PT Reagent Lots Manufactured Using Exemplary Methods According to the Present Invention

| rTF-based PT Reagent Lot Number | rTF Concentration (U/L) in the TF/Phospholipid mixture | Inorganic Phosphate Concentration (mM) | ISI | MNPT (seconds) | Pass/Fail |
|---|---|---|---|---|---|
| 15 | 9,056 | 2.5 | 1.18 | 7.93 | P |
| 16 | 9,056 | 2.5 | 1.15 | 7.80 | P |
| 17 | 9,056 | 2.5 | 1.15 | 8.07 | P |
| 18 | 13,500 | 3.9 | 1.11 | 7.39 | P |
| 19 | 13,500 | 3.2 | 1.16 | 7.42 | P |
| 20 | 13,500 | 3.9 | 1.09 | 7.44 | P |
| 21 | 13,500 | 3.9 | 1.11 | 7.88 | P |
| 22 | 13,500 | 3.6 | 1.14 | 7.59 | P |
| 23 | 13,500 | 3.6 | 1.11 | 7.71 | P |
| 24 | 13,500 | 3.2 | 1.19 | 7.72 | P |

TABLE 3-continued

Summary of ISI and MNPT for rTF-based PT Reagent Lots Manufactured Using Exemplary Methods According to the Present Invention

| rTF-based PT Reagent Lot Number | rTF Concentration (U/L) in the TF/Phospholipid mixture | Inorganic Phosphate Concentration (mM) | ISI | MNPT (seconds) | Pass/Fail |
|---|---|---|---|---|---|
| 25 | 18,000 | 3.8 | 1.10 | 7.48 | P |
| 26 | 13,500 | 3.2 | 1.15 | 7.64 | P |
| 27 | 13,500 | 3.7 | 1.14 | 7.93 | P |
| 28 | 13,500 | 3.9 | 1.11 | 7.58 | P |
| 29 | 13,500 | 3.4 | 1.13 | 7.65 | P |

Based on the data of Table 3, suitable rTF activity concentrations are in the range of 9,000 to 13,500, while suitable phospholipid concentrations are in the range of 2.5 to 3.9 mM. Various ratios of added rTF activity and phosphate concentration that may be of interest to those skilled in the art can be routinely derived from the data of Tables 2 and 3. However, is believed that employing predetermined concentration ranges for added TF activity and phospholipid is sufficient in terms of reproducibly yielding a suitably sensitive TF-based PT reagent.

Figure 2:
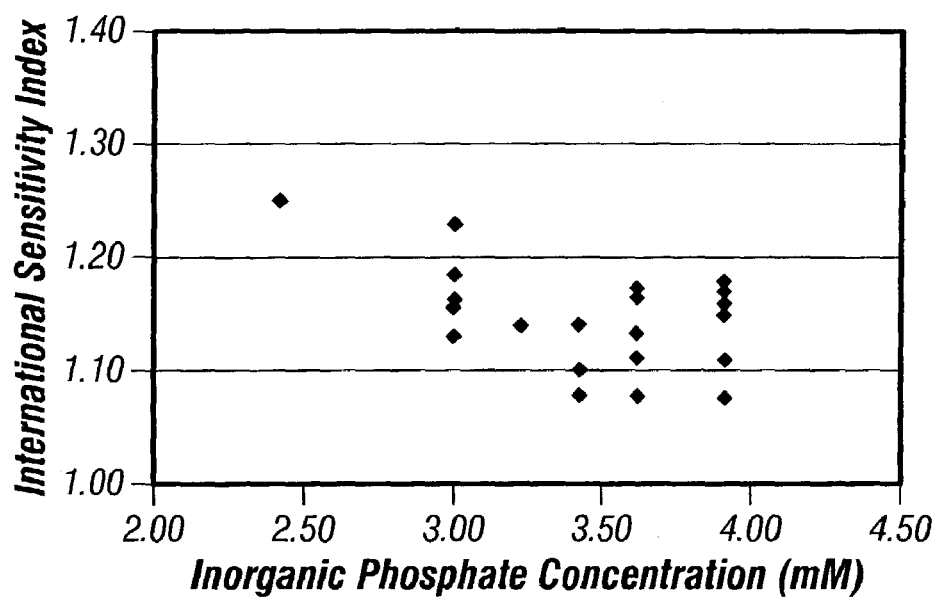
FIG. 2 is a graph showing the effect of phospholipid concentration on International Sensitivity Index.
Figure 3:
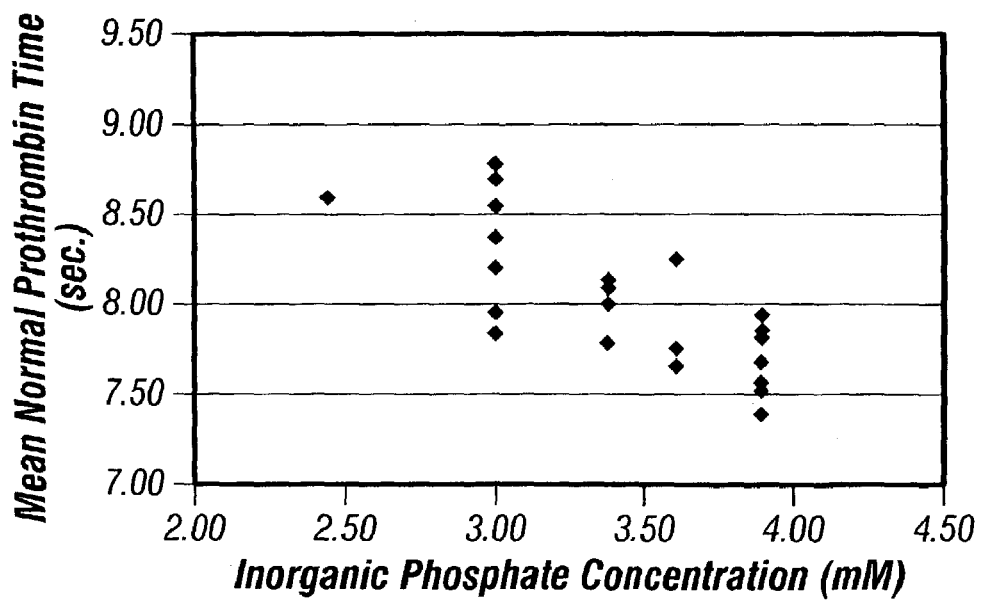
FIG. 3 is a graph showing the effect of phospholipid concentration on Mean Normal Prothrombin Time.

The effect of the phospholipid concentration (measured as inorganic phosphate) on ISI and MNPT at a constant concentration of rTF are shown in FIGS. 2 and 3, respectively. FIG. 2 demonstrates that when the inorganic phosphate concentration is in the range of approximately 2.5 and 3.9 mM, the ISI is within the desired range of 1.0 to 1.3. As shown in FIG. 3, the same inorganic phosphate concentration range also results in an MNPT within a desired range of 7.0 to 9.0 seconds.

It should be understood that various alternatives to the embodiments of the invention described herein may be employed in practicing the invention. It is intended that the following claims define the scope of the invention and that methods within the scope of these claims and their equivalents be covered thereby.

What is claimed is:

1. A method for manufacturing a tissue factor-based prothrombin time (PT) reagent, the method comprising:
combining predetermined quantities of tissue factor (TF), phospholipids and detergent-containing buffer to create a TF/phospholipids mixture, wherein the predetermined quantity of TF is based on a measured activity of TF to function as a cofactor for factor VIIa; and
removing the detergent from the TF/phospholipids mixture to create an essentially detergent-free TF/phospholipids vesicle mixture, thereby creating a tissue factor-based PT reagent.

2. The method of claim 1, wherein the combining step includes adding the predetermined quantity of TF to a mixture of phospholipids and detergent-containing buffer.

3. The method of claim 1, wherein the combining step includes adding a predetermined quantity of recombinant tissue factor (rTF).

4. The method of claim 1, wherein the removing step is accomplished using a technique that includes:
adding a hydrophobic resin to the TF/phospholipids mixture; incubating the TF/phospholipids mixture and the added resin until the TF/phospholipids mixture is essentially free of detergent; and removing said hydrophobic resin from the TF/phospholipids mixture.

5. The method of claim 4, wherein the removing step is accomplished using a technique that further includes the step of prescreening the hydrophobic resin prior to the adding step based on solubilized phospholipids recovery.

6. The method of claim 5, wherein the prescreening includes prescreening the hydrophobic resin based on solubilized phospholipids recovery in the range of 75% to 95%.

7. The method of claim 1 further comprising the steps of:
measuring the total phospholipids concentration of the essentially detergent-free TF/phospholipids vesicle mixture; and
determining acceptability of the essentially detergent-free TF/phospholipids vesicle mixture for use as a tissue factor-based PT reagent based on the measured total phospholipids concentration.

8. The method of claim 7, wherein the measuring step measures the phospholipids concentration in terms of inorganic phosphate concentration and the determining step includes accepting for use tissue factor-based PT reagent with a measured total phospholipids concentration in the range of 2.5 to 5.0 Mm in terms of inorganic phosphate concentration.

9. The method of claim 1, wherein the TF functional activity is measured by a fluorogenic TF activity assay.

10. The method of claim 9, wherein the fluorogenic TF activity assay utilizes a 6-peptidylamino-1-naphthalenesulfonamide fluorogenic substrate.

11. The method of claim 10, wherein the combining step combines a predetermined quantity of TF such that a TF activity of the TF/phospholipids mixture is in the range of 9,000 units to 18,000 units per liter.

* * * * *